United States Patent
Wu et al.

(10) Patent No.: US 8,534,297 B1
(45) Date of Patent: Sep. 17, 2013

(54) METHOD OF TESTING MOISTURE RETENTION OF TOBACCO

(75) Inventors: Da Wu, Shanghai (CN); Guoqiang Zong, Shanghai (CN); Chaoying Chen, Shanghai (CN); Baizhan Liu, Shanghai (CN)

(73) Assignee: Shanghai Tobacco Group Co., Ltd., Shanghai (CN)

( * ) Notice: Subject to any disclaimer, the term of this patent is extended or adjusted under 35 U.S.C. 154(b) by 0 days.

(21) Appl. No.: 13/393,127

(22) PCT Filed: Dec. 16, 2010

(86) PCT No.: PCT/CN2010/079897
§ 371 (c)(1),
(2), (4) Date: Feb. 28, 2012

(87) PCT Pub. No.: WO2012/065330
PCT Pub. Date: May 24, 2012

(30) Foreign Application Priority Data

Nov. 16, 2010 (CN) .......................... 2010 1 0548696

(51) Int. Cl.
*A24B 3/10* (2006.01)
(52) U.S. Cl.
USPC ............................ 131/290; 131/300; 131/303
(58) Field of Classification Search
USPC ......................................... 131/290, 300, 303
See application file for complete search history.

(56) References Cited

U.S. PATENT DOCUMENTS 6,107,809 A * 8/2000 Moshe et al. ................. 324/640

OTHER PUBLICATIONS

CN 101393099, DERWENT English Abstract (and associated Drawing), DERWENT-ACC No: 2009-G80665, Ceng et al, Mar. 25, 2009.*

* cited by examiner

*Primary Examiner* — Richard Crispino
*Assistant Examiner* — Dionne Walls Mayes
(74) *Attorney, Agent, or Firm* — Ming Chow; Sinorica, LLC

(57) ABSTRACT

The present invention provides a method of testing moisture retention of tobacco in which dynamic rules on moisture desorption of the cut tobacco in a dry environment are investigated by using a dynamic vapor sorption system and has found that a dry basis moisture content at an earlier stage of moisture desorption of the cut tobacco has a preferred linear correlation with a square root of time. A linear fitting for $t^{0.5}$ is made by using values of a dry basis moisture content Mt at a time point t, and a rate constant k is obtained from a slop of the obtained straight line and used as a reference of testing the moisture retention of tobacco. The method can also be used to investigate the moisture retention of tobacco and filter humectants of cigarettes. In comparison with the conventional method, the method is convenient and applicable, and has a short testing period, a high degree of automation, preferred accuracy and preferred reproducibility, etc.

12 Claims, 5 Drawing Sheets

METHOD OF TESTING MOISTURE RETENTION OF TOBACCO

BACKGROUND OF THE PRESENT INVENTION

1. Field of Invention

The present invention relates to a new method of testing and evaluating physical moisture retention of tobacco.

2. Description of Related Arts

The moisture retention of cigarettes has a rather close relationship with the quality of the cigarettes, and the particular study on fragrance enhancement and moisture retention of cigarettes is important in the Mid-Term and Long-Term Science and Technology Development Plan of tobacco industry. A problem firstly encountered in studying the moisture retention of the cigarettes is how to test and evaluate the moisture retention accurately and conveniently. Currently, the following evaluation method is commonly used. Specifically, a cut tobacco sample without any humectant and a cut tobacco sample with humectants added are put into a drier having a saturated saline solution inside or a thermo-hygrostat and then are weighed periodically. Next, moisture contents of the samples at different time points are calculated by using an oven method and compared by drawing a graph. However, the above evaluation method generally has the following disadvantages. (1) The testing period is long, and the method is complicated. The testing method generally needs 3 to 5 days to enable the tobacco samples to reach equilibrium moisture content, and requires large numbers of repeated manual operations. (2) The tobacco belongs to colloid capillary porous thin-layer materials and has a relatively strong water absorbability, so the testing result tends to be affected by operators and operating environments, therefore causing that the result may not be accurate and has poor reproducibility. (3) Only some discontinuous data points are obtained which fail to reflect tiny changes in the moisture contents of the tobacco samples against time, therefore making it difficult to investigate dynamic rules of moisture desorption or moisture absorption of the cut tobacco. Accordingly, it is urgent to provide a new method of testing the moisture retention of tobacco logically and effectively.

On the other hand, various novel dynamic vapor sorption (DVS) instruments are being constantly developed, and have been successfully applied in various related fields such as pharmaceutical industry, food industry, and material industry. The instruments can control relative humidity and temperature of tested samples accurately and conveniently, and have greatly improved precision and accuracy in comparison with the conventional method using the saturated saline solution.

SUMMARY OF THE PRESENT INVENTION

In view of the above technical problems existent in the prior art, an objective of the present invention is to provide a method suitable for testing moisture retention of tobacco.

Dynamic rules of moisture-desorption of cut tobacco in a dry environment are studied in the present invention by using a dynamic vapor sorption system, and results indicate that a dry basis moisture content at an earlier stage of moisture-desorption of the cut tobacco has a preferred linear correlation with a square root of time. From a slope of the thus-obtained straight line, a value of a rate constant k is obtained as a reference of testing the moisture retention of tobacco. This method can also be used to investigate the moisture retention of tobacco and filter humectant of cigarettes. In comparison with the conventional method, this method is convenient and applicable, and has a short testing period, high degree of automation, preferred accuracy, and preferred reproducibility, etc.

The present invention provides the following technical solutions to solve the above technical problems.

The present invention provides a method of testing moisture retention of tobacco which includes the following steps:

Step One of pretreating samples in which a cut tobacco sample is placed into a thermo-hygrostat for 48 hours to 72 hours to reach equilibrium for use;

Step Two in which a predetermined amount of the cut tobacco sample to be tested is weighed, weight changes against time t of the cut tobacco sample is tested at a predetermined temperature in a dry environment, a dry basis weight of the cut tobacco sample is measured after reaching a predetermined equilibrium moisture content, and based on the measured dry basis weight as well as a curve showing the weight changes against time of the cut tobacco sample, a dry basis moisture content Mt of the cut tobacco sample at a time point t is calculated for drawing a curve showing changes in the dry basis moisture content Mt against the time t;

Step Three in which, during a time period when the dry basis moisture content satisfies $0.4<Mt-Me/M_0-Me<1.0$, a dry basis moisture content value at a time point t is obtained from the curve showing changes in the dry basis moisture content Mt against the time t in Step Two and is used for drawing a line diagram for $t^{0.5}$ the slop of which is a rate constant k of moisture desorption, wherein $M_0$ is the dry basis moisture content of the cut tobacco at the initial time point, Mt is the dry basis moisture content of the cut tobacco at the time point t, and Me is the dry basis moisture content of the cut tobacco reaching the equilibrium moisture content; and Step Four in which a cut tobacco sample with humectants added and a blank sample for comparison are respectively subjected to the above testing to obtain a moisture-desorption rate constant k in the dry environment, and the moisture retention of the tobacco humectant is determined according to a value of the k.

In Step One, a temperature and a degree of humidity in the thermo-hygrostat depend on initial equilibrium conditions of the experiment.

In Step Two, the predetermined temperature is in the range of 15° C. to 40° C.

In Step Two, the amount of the cut tobacco sample is in the range of 1.000 g to 2.000 g.

In Step Two, the dry environment has a relative humidity of 20% to 40%.

In Step Two, the dry basis weight of the cut tobacco sample is measured by using an oven method in which a sample basket is placed into an oven and dried for 2 hours at 100° C., and then is cooled in a drier and weighed by an analytical balance to obtain the dry basis weight.

In Step Two, a dynamic vapor sorption system is used to measure the weight changes against the time t of the cut tobacco sample in the dry environment, and an equilibrium control mode of the dynamic vapor sorption system is set as a time control mode or a speed control mode.

In Step Three, in the time period when the dry basis moisture content Mt satisfies $0.4<Mt-Me/M_0-Me<1.0$, a correlation model between the dry basis moisture content Mt of the cut tobacco and the time t is $Mt=k \times t^{0.5}+M_0$, wherein $M_0$ is the dry basis moisture content of the cut tobacco at the initial time point, Mt is the dry basis moisture content of the cut tobacco at the time point t, and Me is the dry basis moisture content of the cut tobacco reaching the equilibrium moisture content.

The present invention has the following merits.

1) A correlation model between the time and the dry basis moisture content of the cut tobacco in a short time is established, and it is proposed to use the value of the rate constant as a reference of evaluating the moisture retention of the tobacco and the moisture retention of the humectant;

2) In comparison with the usual testing period of 3 days to 5 days, the present invention has a testing period reduced to 16 hours to 20 hours;

3) The present invention is convenient and applicable and after the sample is provided, a computer automatically finishes a series of operations such as weighing and recording under at a predetermined temperature and a predetermined degree of humidity, showing that the present invention has a high degree of automation;

4) The present invention has preferred accuracy and reproducibility. Specifically, a relative standard bias of results of five experiments performed under the same conditions is less than 1.5%, and tiny changes in the moisture content of the tobacco samples against the time may be reflected, thereby facilitating the study of dynamic rules on dehydration or moisture absorption of the cut tobacco.

DETAILED DESCRIPTION OF THE PREFERRED EMBODIMENTS

Figure 1:
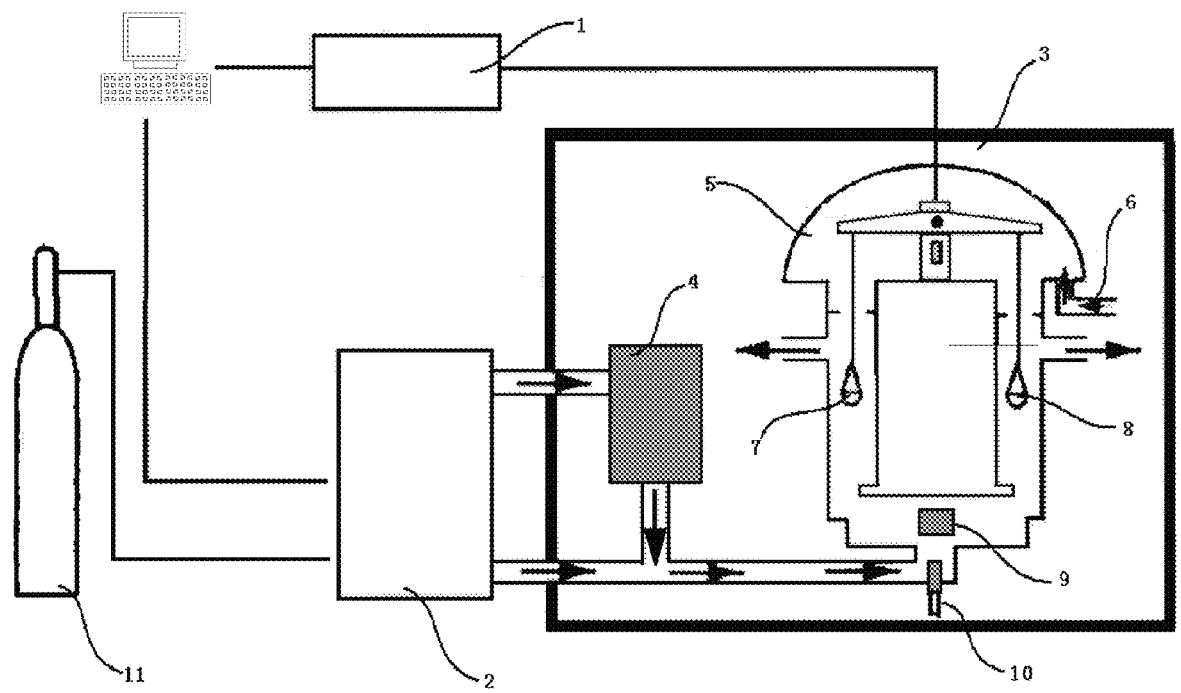
FIG. 1 is a schematic view of an apparatus used in the present invention, wherein the reference numeral 1 refers to a balance controller, 2 refers to a flow controller, 3 refers to a thermotank, 4 indicates a temperature generator, 5 refers to an ultramicrobalance, 6 refers to a balance protection gas, 7 refers to a sample plate, 8 refers to a reference plate, 9 refers to a DPA, 10 refers to a temperature probe, and 11 refers to a $N_2$ cylinder.

A schematic frame diagram of a DVS apparatus used in the present invention is shown in FIG. 1. The system includes an ultramicrobalance 5, a gas flow controller 2, etc. A main portion of the apparatus is placed in a temperature controllable thermotank 3, the electronic balance in the middle part is placed in a separated isolation area, and a vapor generator is mounted in the rear part of the apparatus. A computer is connected to the gas flow controller 2 and the balance controller 1 respectively via a data collecting card and an RS-232 serial port. During the operation of the apparatus, a flow rate of a dry carrier gas and a flow rate of a saturated vapor carrier gas are controlled by the gas flow controller 2 to be mixed to form a series of gas flows of a predetermined humidity which then flow through a sample to be tested and a reference area, so that a state of equilibrium reach equilibrium is reached in a moisture absorption or desorption experiment. A temperature probe 10 and a DPA 9 are used to control temperatures and a relative humidity of the gas flowing through the sample. The computer records in real time changes of a weight of the sample at different humidity and different time via the electronic balance.

The samples are subjected to a sample pretreatment process. Specifically, cut tobacco samples used in the following embodiments are respectively cut into a unified shape and mixed uniformly, and then are placed into a thermo-hygrostat (22° C., relative humidity: 60%±1%) for 48 hours to reach equilibrium for use.

Embodiment 1

Figure 2:
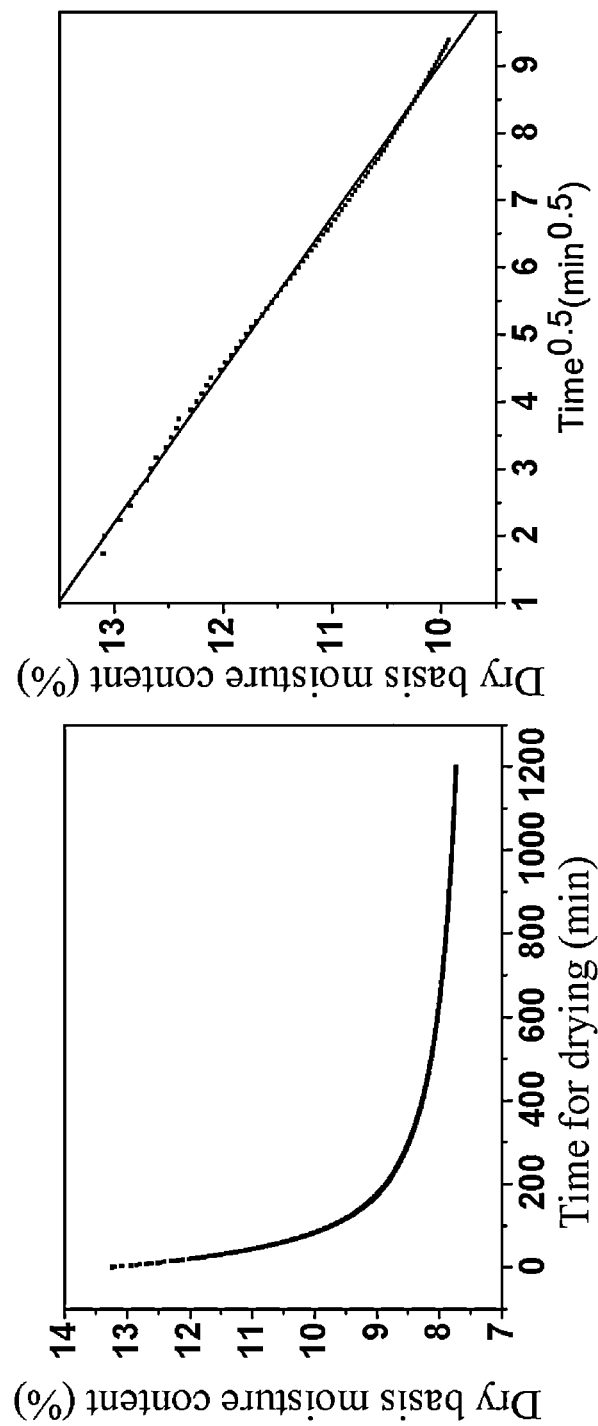
FIG. 2 is a curve showing changes in dry basis moisture content against time with respect to a cut tobacco A and a linear fitting thereof ($0.4 < Mt-Me/M_0-Me < 1.0$).

1.000 g of a cut tobacco sample A to be tested was weighed by using an analytical balance, and then was spread flatly on a sample basket (whose inner diameter was 27 mm) of a microbalance of the DVS system. After reaching equilibrium at a relative humidity of 60%, weight changes against time of the cut tobacco sample A in a dry environment having a relative humidity of 33% were investigated with the equilibrium control mode set as a time control mode (Time=20 h). The computer recorded automatically the weight of the sample every 1 minute, and the apparatus stopped weighing after the cut tobacco sample A reached the equilibrium moisture content. The sample basket was placed in an oven and dried for 2 hours at 100° C. with reference to the oven method, and a dry basis weight of the sample was obtained by using the analytical balance to weigh the sample. Based on the dry basis weight as well as a curve showing the weight changes of the tested sample against the time, values of dry basis moisture content at corresponding time points were calculated for drawing a FIG. (see FIG. 2) with the number of repeated testing to be 5, a rate constant $k_1$ to be $-437\%/min^{1/2}$, a fit coefficient $R^2$ to be greater than 0.998, and a relative standard bias of reproducibility testing RSD to be less than 1.0%.

Embodiment 2

Figure 3:
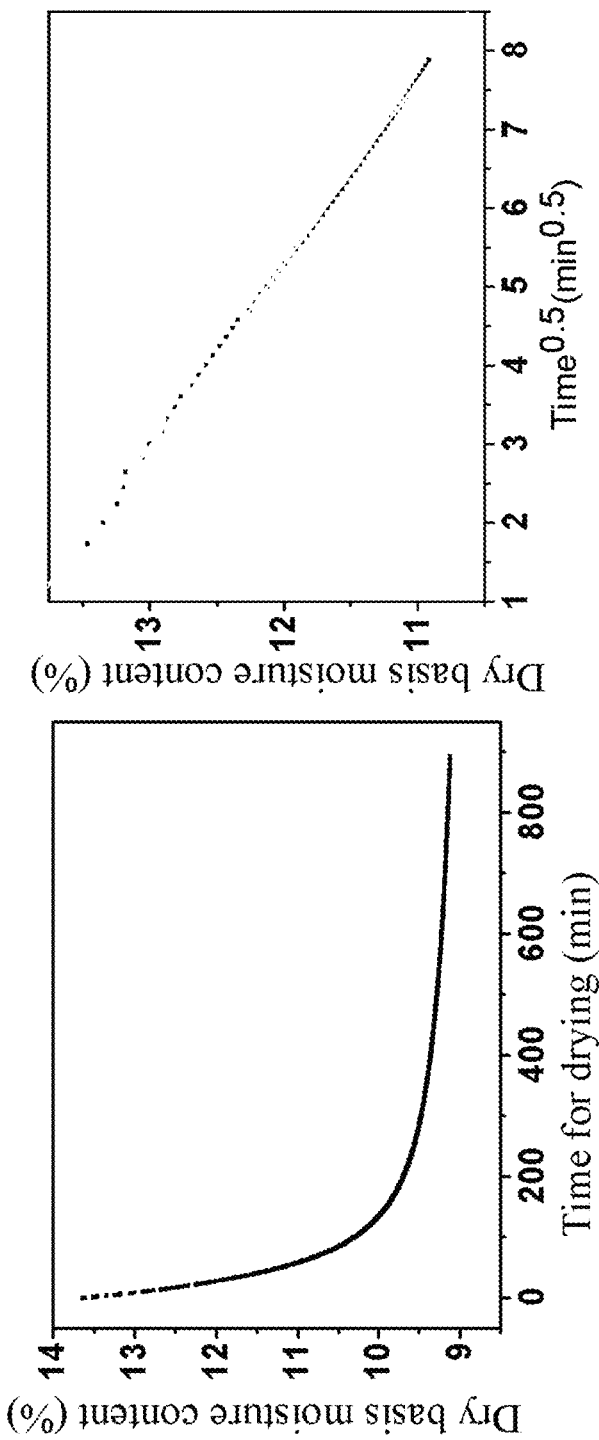
FIG. 3 is a curve showing changes in dry basis moisture content against time with respect to a cut tobacco B and a linear fitting thereof ($0.4 < Mt-Me/M_0-Me < 1.0$).

1.000 g of a cut tobacco sample B to be tested was weighed by using the analytical balance, and then was spread flatly on the sample basket (whose inner diameter was 27 mm) of the microbalance of the DVS system. After reaching equilibrium at the relative humidity of 60%, weight changes against time of the cut tobacco B in a dry environment having the relative humidity of 33% were investigated with the equilibrium control mode set as a speed control mode (dm/dt Mode) dm/dt=0.0002 (%/min). The computer recorded automatically the weight of the sample every 1 minute, and the apparatus stopped weighing after the sample tobacco reached the equilibrium moisture content. The sample basket was placed into the oven and dried for 2 hours at 100° C. with reference to the oven method, and a dry basis weight of the sample was obtained by using the analytical balance to weigh the sample. Based on the dry basis weight as well as a curve showing weight changes of the tested sample against time, values of dry basis moisture content at corresponding time points were calculated for drawing a figure (see FIG. 3) with the number of repeated testing to be 5, a rate constant $k_2$ to be $-0.429\%/min^{1/2}$, a fit coefficient $R^2$ to be greater than 0.998, and a relative standard bias of reproducibility testing RSD to be less than 1.0%.

Embodiment 3

Figure 4:
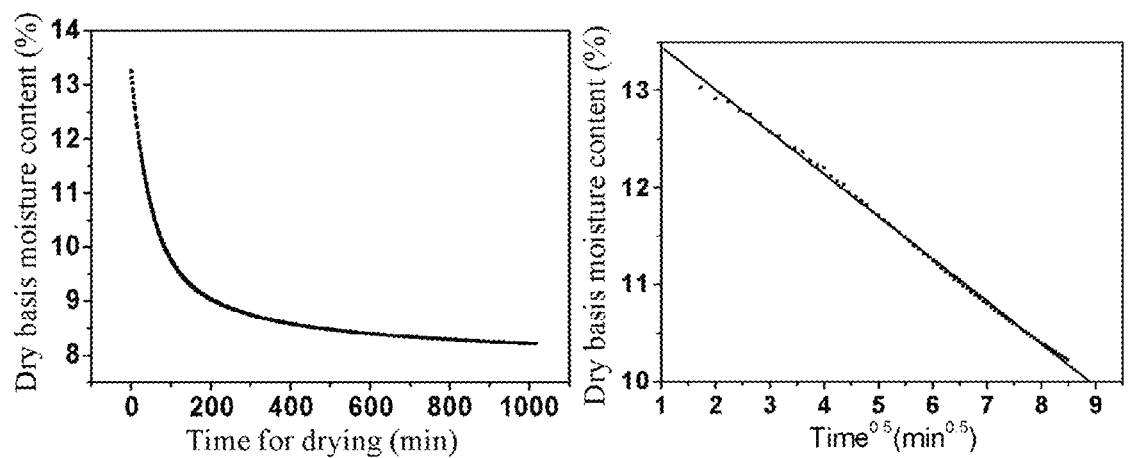
FIG. 4 is a curve showing changes in dry basis moisture content against time with respect to a cut tobacco C and a linear fitting thereof ($0.4 < Mt-Me/M_0-Me < 1.0$).

1.200 g of a cut tobacco sample C to be tested were weighed by using the analytical balance and then were spread flatly on the sample basket (whose inner diameter was 27 mm) of the microbalance of the DVS system. After reaching equilibrium at a relative humidity of 60%, weight changes against time of the cut tobacco D in a dry environment having the relative humidity of 33% were investigated with the equilibrium control mode set as a speed control mode (dm/dt Mode) dm/dt=0.0002 (%/min). The computer recorded automatically the weight of the sample every 1 minute, and the apparatus stopped weighing after the sample tobacco reached the equilibrium moisture content. The sample basket was placed into the oven and dried for 2 hours at 100° C. with reference to the oven method, and a dry basis weight of the sample was obtained by using the analytical balance to weigh. Based on the dry basis weight and a curve showing weight changes of the tested sample against time, values of dry basis moisture content at corresponding time points were calculated for drawing a figure (see FIG. 4) with the number of repeated testing n to be 5, a rate constant $k_3$ to be −0.435%/min$^{1/2}$, a fit coefficient $R^2$ to be greater than 0.998, and a relative standard bias of reproducibility testing RSD to be less than 1.0%.

Embodiment 4

Figure 5:
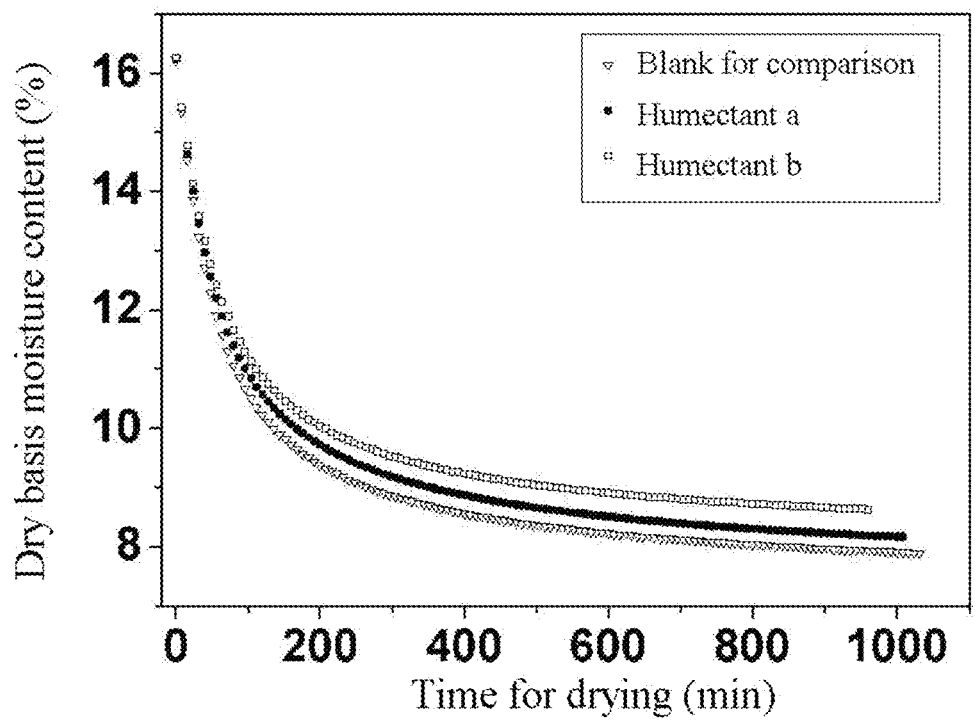
FIG. 5 is curves showing changes in dry basis moisture content against time with respect to a cut tobacco D without humectants and with respect to the cut tobacco D with humectants a and b added respectively, and linear fittings thereof ($0.4 < Mt-Me/M_0-Me < 1.0$).
Figure 5:
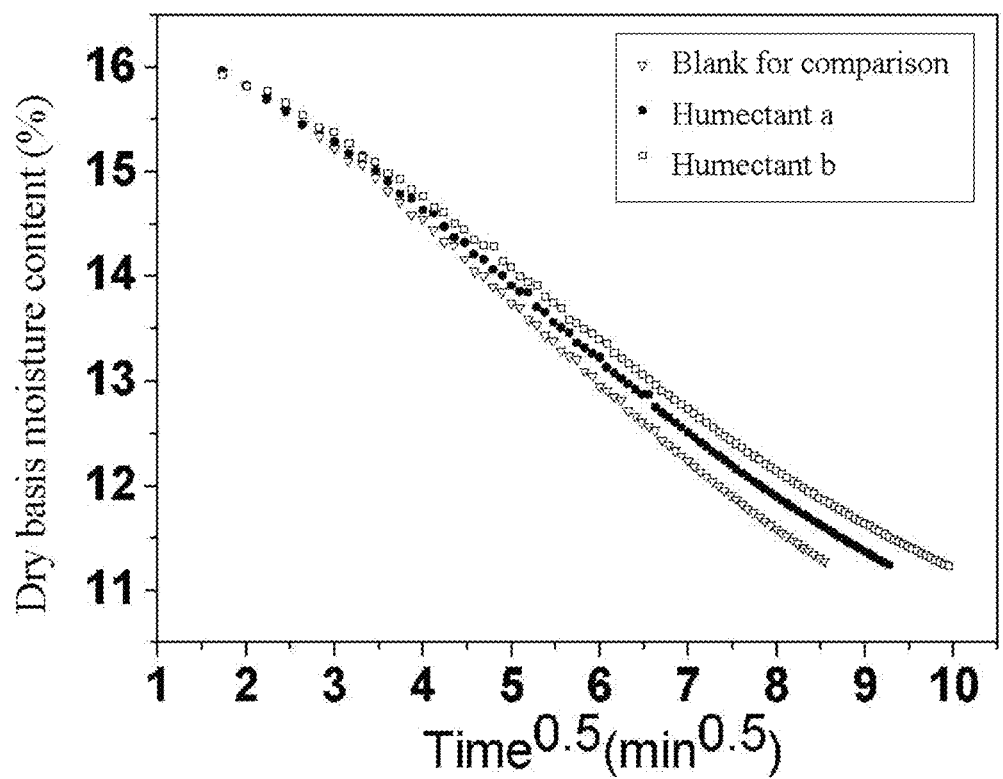

50 g of cut tobacco D were weighed and then sprayed with 1.0 g of a humectant and 2.5 g of water, and a sample for comparison was sprayed with 3.5 g water. Hereinafter, the sample sprayed with water only is referred to as the blank sample for comparison. The samples were then placed into the thermo-hygrostat (22° C., relative humidity: 60%±1%) for 72 hours to reach equilibrium. 1.000 g of the cut tobacco samples to be tested was weighed by using the analytical balance and then spread flatly on the sample basket (whose inner diameter was 39 mm) of the microbalance of the DVS system. After reaching equilibrium at the relative humidity of 60%, weight changes against time of the cut tobacco samples in a dry environment having the relative humidity of 33% were investigated with the equilibrium control mode set as a speed control mode (dm/dt Mode) dm/dt=0.0005 (%/min). The computer recorded automatically weights of the samples every 1 minute, and the apparatus stopped weighing after the cut tobacco samples reached the equilibrium moisture content. The sample basket was placed into the oven and dried for 2 hours at 100° C. with reference to the oven method, and dry basis weights of the samples were obtained by using the analytical balance to weigh the samples. Based on the dry basis weight as well as a curve showing weight changes of the tested samples against time, values of dry basis moisture content at corresponding time points of the blank sample for comparison and of the cut tobacco samples with the humectant a and b added were calculated respectively for drawing FIGS. showing changes in the dry basis moisture content within the same interval as that of the blank sample for comparison (see FIG. 5). A comparison was made accordingly and results are as follows:

For the blank sample for comparison, the number of repeated testing n is 5, a rate constant $k_4$ is −0.730%/min$^{1/2}$, RSD is less than 1.0%, and a fit coefficient $R^2$ is greater than 0.998.

For the cut tobacco sample D with the humectant a added, the number of repeated testing n is 5, a rate constant $k_{4a}$ is −0.672%/min$^{1/2}$, RSD is less than 1.2%, and a fit coefficient $R^2$ is greater than 0.997.

For the cut tobacco sample D with the humectant b added, the number of repeated testing n is 5, a rate constant $k_{4b}$ is −0.603%/min$^{1/2}$, RSD is less than 1.5%, and a fit coefficient $R^2$ is greater than 0.995.

The relationship between the rate constants is $|k_{4b}|<|k_{4a}|<|k_4|$, indicating that the tobacco humectants b and a both have an obvious physical moisture retention effect, and the humectant b has a physical moisture retention effect better than the humectant a.

What is claimed is:

1. A method of testing moisture retention of tobacco, comprising:

Step One of pretreating samples in which a cut tobacco sample is placed into a thermo-hygrostat for 48 hours to 72 hours to reach equilibrium for use;

Step Two in which a predetermined amount of the cut tobacco sample to be tested is weighed, weight changes against time t of the cut tobacco sample is tested at a predetermined temperature in a dry environment, a dry basis weight of the cut tobacco sample is measured after reaching a predetermined equilibrium moisture content, and based on the measured dry basis weight as well as a curve showing the weight changes against time of the cut tobacco sample, a dry basis moisture content Mt of the cut tobacco sample at a time point t is calculated for drawing a curve showing changes in the dry basis moisture content Mt against the time t;

Step Three in which, during a time period when the dry basis moisture content satisfies 0.4<Mt−Me/M0−Me<1.0, a dry basis moisture content value at a time point t is obtained from the curve showing changes in the dry basis moisture content Mt against the time t in Step Two and is used for drawing a line diagram for t0.5 the slope of which is a rate constant k of moisture desorption, wherein M0 is the dry basis moisture content of the cut tobacco at the initial time point, Mt is the dry basis moisture content of the cut tobacco at the time point t, and Me is the dry basis moisture content of the cut tobacco reaching the equilibrium moisture content; and Step Four in which a cut tobacco sample with humectants added and a blank sample for comparison are respectively subjected to the above testing to obtain a moisture-desorption rate constant k in the dry environment, and the moisture retention of the tobacco humectant is determined according to a value of the k.

2. The method of testing moisture retention of tobacco according to claim 1, wherein the predetermined temperature in Step Two is in the range of 15° C. to 40° C.

3. The method of testing moisture retention of tobacco according to claim 2, wherein, in Step Three, during the time period when the dry basis moisture content Mt satisfies 0.4<Mt−Me/M$_0$−Me<1.0, a correlation model between the dry basis moisture content Mt of the cut tobacco and the moisture retention time t is Mt=k×t$^{0.5}$+M$_0$.

4. The method of testing moisture retention of tobacco according to claim 1, wherein the predetermined amount of the cut tobacco sample in Step Two is in the range of 1.000 g to 2.000 g.

5. The method of testing moisture retention of tobacco according to claim 4, wherein, in Step Three, during the time period when the dry basis moisture content Mt satisfies 0.4<Mt−Me/M$_0$−Me<1.0, a correlation model between the dry basis moisture content Mt of the cut tobacco and the moisture retention time t is Mt=k×t0 5+M$_0$.

6. The method of testing moisture retention of tobacco according to claim 1, wherein the dry environment in Step Two has a relative humidity of 20% to 40%.

7. The method of testing moisture retention of tobacco according to claim 6, wherein, in Step Three, during the time period when the dry basis moisture content Mt satisfies 0.4<Mt−Me/M$_0$−Me<1.0, a correlation model between the dry basis moisture content Mt of the cut tobacco and the moisture retention time t is Mt=k×t$^{0.5}$+M$_0$.

8. The method of testing moisture retention of tobacco according to claim 1, wherein, in Step Two, a dynamic vapor sorption system is used to measure the weight changes of the cut tobacco sample against the time t in the dry environment.

9. The method of testing moisture retention of tobacco according to claim 8, wherein, in Step Two, an equilibrium control mode of the dynamic vapor sorption system is set as a time control mode or a speed control mode.

10. The method of testing moisture retention of tobacco according to claim 9, wherein, in Step Three, during the time period when the dry basis moisture content Mt satisfies $0.4 < Mt-Me/M_0-Me < 1.0$, a correlation model between the dry basis moisture content Mt of the cut tobacco and the moisture retention time t is $Mt = k \times t^{0.5} + M_0$.

11. The method of testing moisture retention of tobacco according to claim 8, wherein, in Step Three, during the time period when the dry basis moisture content Mt satisfies $0.4 < Mt-Me/M_0-Me < 1.0$, a correlation model between the dry basis moisture content Mt of the cut tobacco and the moisture retention time t is $Mt = k \times t^{0.5} + M_0$.

12. The method of testing moisture retention of tobacco according to claim 1, wherein, in Step Three, during the time period when the dry basis moisture content Mt satisfies $0.4 < Mt-Me/M_0-Me < 1.0$, a correlation model between the dry basis moisture content Mt of the cut tobacco and the moisture retention time t is $Mt = k \times t^{0.5} + M_0$.

* * * * *